(12) United States Patent
Baerveldt et al.

(10) Patent No.: US 11,744,735 B2
(45) Date of Patent: *Sep. 5, 2023

(54) DEVICES, SYSTEMS AND METHODS FOR MINIMALLY INVASIVE GLAUCOMA SURGERY

(71) Applicant: MICROSURGICAL TECHNOLOGY, INC., Redmond, WA (US)

(72) Inventors: George Baerveldt, Monarch Beach, CA (US); John T. Sorensen, Lake Elsinore, CA (US); Michael Mittelstein, Laguna Niguel, CA (US); Soheila Mirhashemi, Laguna Niguel, CA (US)

(73) Assignee: MICROSURGICAL TECHNOLOGY, INC., Redmond, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/572,835

(22) Filed: Jan. 11, 2022

(65) Prior Publication Data

US 2022/0133539 A1 May 5, 2022

Related U.S. Application Data

(63) Continuation of application No. 15/932,355, filed on Feb. 16, 2018, now Pat. No. 11,266,527.

(60) Provisional application No. 62/584,613, filed on Nov. 10, 2017, provisional application No. 62/460,061, filed on Feb. 16, 2017.

(51) Int. Cl.
*A61F 9/007* (2006.01)
*A61F 9/008* (2006.01)

(52) U.S. Cl.
CPC ...... *A61F 9/00781* (2013.01); *A61F 9/00736* (2013.01); *A61F 2009/00868* (2013.01); *A61F 2009/00891* (2013.01)

(58) Field of Classification Search
CPC .............. A61F 9/00736; A61F 9/00763; A61F 9/00781
See application file for complete search history.

(56) References Cited

U.S. PATENT DOCUMENTS

| 421,855 A | 2/1890 | Burk |
| 637,463 A | 11/1899 | Hegerty |
| 2,130,949 A | 9/1938 | Collens |
| 2,220,169 A | 11/1940 | Murdock |
| 2,364,333 A | 12/1944 | Wisher |
| 3,294,085 A | 12/1966 | Wallace |

(Continued)

FOREIGN PATENT DOCUMENTS

| CN | 102238926 | 11/2011 |
| CN | 101732125 | 7/2012 |

(Continued)

OTHER PUBLICATIONS

Anderson, D.R. "Trabeculolomy Compared to Goniotomy for Glaucoma in Children", Ophthalmology 90(7), 1983, pp. 805-806.

(Continued)

*Primary Examiner* — Adam Marcetich
*Assistant Examiner* — Meagan Ngo
(74) *Attorney, Agent, or Firm* — DLA PIPER LLP (US)

(57) ABSTRACT

Devices and methods useable for forming opening in trabecular meshwork of mammalian eyes.

24 Claims, 9 Drawing Sheets

(56) References Cited

U.S. PATENT DOCUMENTS

| | | |
|---|---|---|
| 3,365,798 A | 1/1968 | Cunningham |
| 3,776,238 A | 12/1973 | Peyman et al. |
| 3,882,872 A | 5/1975 | Douvas et al. |
| 3,972,117 A | 8/1976 | Fogg |
| 4,011,869 A | 3/1977 | Seiler, Jr. |
| 4,111,207 A | 9/1978 | Seiler, Jr. |
| 4,255,854 A | 3/1981 | Bilbao |
| 4,365,957 A | 12/1982 | Das |
| 4,428,748 A | 1/1984 | Peyman et al. |
| 4,472,879 A | 9/1984 | Sizemore, Jr. |
| 4,501,274 A | 2/1985 | Skjaerpe |
| 4,559,942 A | 12/1985 | Eisenberg |
| 4,577,629 A | 3/1986 | Martinez |
| 4,649,919 A | 3/1987 | Thimsen et al. |
| 4,682,597 A | 7/1987 | Myers |
| 4,689,040 A | 8/1987 | Thompson |
| 4,706,669 A | 11/1987 | Schlegel |
| 4,712,546 A | 12/1987 | Noe |
| 4,753,234 A | 6/1988 | Martinez |
| 4,759,746 A | 7/1988 | Straus |
| 4,841,984 A | 6/1989 | Armeniades et al. |
| 4,900,300 A | 2/1990 | Lee |
| 4,955,883 A | 9/1990 | Nevyas et al. |
| 4,955,887 A | 9/1990 | Zirm |
| 5,019,035 A | 5/1991 | Missirlian et al. |
| 5,042,008 A | 8/1991 | Iwasa et al. |
| 5,112,299 A | 5/1992 | Pascaloff |
| 5,123,904 A | 6/1992 | Shimomura et al. |
| 5,163,433 A | 11/1992 | Kagawa et al. |
| 5,222,959 A | 6/1993 | Anis |
| 5,224,950 A | 7/1993 | Prywes |
| 5,269,782 A | 12/1993 | Sutter |
| 5,284,472 A | 2/1994 | Sussman et al. |
| 5,431,646 A | 7/1995 | Vassiliadis et al. |
| 5,431,671 A | 7/1995 | Nallakrishnan |
| 5,458,596 A | 10/1995 | Lax et al. |
| 5,478,338 A | 12/1995 | Reynard |
| 5,487,747 A | 1/1996 | Stagmann et al. |
| 5,529,580 A | 6/1996 | Kusunoki et al. |
| 5,540,706 A | 7/1996 | Aust et al. |
| 5,540,708 A | 7/1996 | Lim et al. |
| 5,558,637 A | 9/1996 | Allonen et al. |
| 5,569,283 A | 10/1996 | Green et al. |
| 5,620,453 A | 4/1997 | Nallakrishnan |
| 5,674,233 A | 10/1997 | Dybbs |
| 5,681,282 A | 10/1997 | Eggers et al. |
| 5,713,915 A | 2/1998 | Van Heugten et al. |
| 5,733,297 A | 3/1998 | Wang |
| 5,755,716 A | 5/1998 | Garito et al. |
| 5,807,277 A | 9/1998 | Swaim |
| 5,817,115 A | 10/1998 | Nigam |
| 5,843,106 A | 12/1998 | Heisler |
| 5,865,831 A | 2/1999 | Cozean et al. |
| 5,885,279 A | 3/1999 | Bretton |
| 5,922,003 A | 7/1999 | Anctil et al. |
| 5,957,881 A | 9/1999 | Peters et al. |
| 5,957,914 A | 9/1999 | Cook et al. |
| 5,964,777 A | 10/1999 | Drucker |
| 6,004,199 A | 12/1999 | Habenicht et al. |
| 6,013,049 A | 1/2000 | Reckley et al. |
| 6,068,629 A | 5/2000 | Haissaguerre et al. |
| 6,139,559 A | 10/2000 | Nordan et al. |
| 6,213,997 B1 | 4/2001 | Hood et al. |
| 6,217,598 B1 | 4/2001 | Berman et al. |
| 6,241,721 B1 | 6/2001 | Cozean et al. |
| 6,251,103 B1 | 6/2001 | Berlin |
| 6,264,668 B1 | 7/2001 | Prywes |
| 6,283,961 B1 | 9/2001 | Underwood et al. |
| 6,290,699 B1 | 9/2001 | Hall et al. |
| 6,293,957 B1 | 9/2001 | Peters et al. |
| 6,382,974 B1 | 5/2002 | Garfinkel |
| 6,388,043 B1 | 5/2002 | Langer et al. |
| 6,419,684 B1 | 7/2002 | Heisler et al. |
| 6,428,501 B1 | 8/2002 | Reynard |
| 6,428,539 B1 | 8/2002 | Baxter et al. |
| 6,432,104 B1 | 8/2002 | Durgin et al. |
| 6,497,712 B1 | 12/2002 | Feaster |
| 6,503,262 B1 | 1/2003 | Edens |
| RE38,018 E | 3/2003 | Anctil et al. |
| 6,557,258 B1 | 5/2003 | Roberts et al. |
| 6,720,402 B2 | 4/2004 | Langer et al. |
| 6,759,481 B2 | 7/2004 | Tong |
| 6,979,328 B2 | 12/2005 | Baerveldt et al. |
| 7,131,975 B2 | 11/2006 | Adams |
| 7,244,256 B2 | 7/2007 | Decesare et al. |
| 7,374,566 B1 | 5/2008 | Schossau |
| 7,604,663 B1 | 10/2009 | Reimink et al. |
| 7,632,303 B1 | 12/2009 | Stalker et al. |
| 7,648,591 B2 | 1/2010 | Furst et al. |
| 7,785,321 B2 | 8/2010 | Baerveldt et al. |
| 7,842,034 B2 | 11/2010 | Mittelstein et al. |
| 7,935,131 B2 | 5/2011 | Anthamatten et al. |
| 7,955,387 B2 | 6/2011 | Richter |
| 7,959,641 B2 | 6/2011 | Sorensen et al. |
| 8,038,923 B2 | 10/2011 | Berger et al. |
| 8,069,546 B1 | 12/2011 | Whittemore |
| 8,147,424 B2 | 4/2012 | Kassab et al. |
| 8,287,560 B2 | 10/2012 | Spaide |
| 8,512,321 B2 | 8/2013 | Baerveldt et al. |
| 8,764,782 B2 | 7/2014 | Akahoshi |
| 9,757,279 B2 | 9/2017 | Kahook |
| 9,872,799 B2 | 1/2018 | Kahook |
| 2001/0034932 A1 | 11/2001 | MacDonald |
| 2001/0053873 A1 | 12/2001 | Schaaf et al. |
| 2002/0002372 A1 | 1/2002 | Jahns et al. |
| 2002/0026205 A1 | 2/2002 | Matsutani et al. |
| 2002/0038129 A1 | 3/2002 | Peters et al. |
| 2002/0111608 A1 | 8/2002 | Baerveldt et al. |
| 2003/0208217 A1 | 11/2003 | Dan |
| 2004/0138685 A1 | 7/2004 | Clague et al. |
| 2004/0153111 A1 | 8/2004 | Hosoada |
| 2004/0204732 A1 | 10/2004 | Muchnik |
| 2004/0210245 A1 | 10/2004 | Erickson et al. |
| 2005/0070941 A1 | 3/2005 | Isogimi |
| 2005/0090849 A1 | 4/2005 | Adams |
| 2005/0113644 A1 | 5/2005 | Obenchain et al. |
| 2005/0131403 A1 | 6/2005 | Chang |
| 2005/0159767 A1 | 7/2005 | Adams et al. |
| 2005/0216019 A1 | 9/2005 | Eckman |
| 2006/0015128 A1 | 1/2006 | Fard |
| 2006/0095055 A1 | 5/2006 | Douglas et al. |
| 2006/0106370 A1 | 5/2006 | Baerveldt et al. |
| 2006/0149194 A1 | 7/2006 | Conston et al. |
| 2006/0149267 A1 | 7/2006 | Nordt |
| 2006/0200180 A1 | 9/2006 | Lee |
| 2006/0212060 A1 | 9/2006 | Hacker et al. |
| 2006/0241580 A1 | 10/2006 | Mittelstein et al. |
| 2006/0271074 A1 | 11/2006 | Ewers et al. |
| 2007/0010812 A1 | 1/2007 | Mittelstein et al. |
| 2007/0073275 A1 | 3/2007 | Conston et al. |
| 2007/0100363 A1 | 5/2007 | Dollar et al. |
| 2007/0149974 A1 | 6/2007 | Mangione |
| 2007/0276420 A1* | 11/2007 | Sorensen ............ A61F 9/00736 606/167 |
| 2008/0021399 A1 | 1/2008 | Spaide |
| 2008/0077146 A1 | 3/2008 | Pernsteiner et al. |
| 2008/0154296 A1 | 6/2008 | Taylor et al. |
| 2009/0112240 A1 | 4/2009 | Slaughter et al. |
| 2009/0248141 A1 | 10/2009 | Shandas et al. |
| 2009/0287233 A1 | 11/2009 | Huculak |
| 2009/0306689 A1 | 12/2009 | Welty et al. |
| 2010/0152609 A1 | 6/2010 | Zwolinski et al. |
| 2010/0268175 A1 | 10/2010 | Lunsford et al. |
| 2011/0077626 A1 | 3/2011 | Baerveldt et al. |
| 2011/0202049 A1 | 8/2011 | Jia et al. |
| 2011/0230877 A1 | 9/2011 | Huculak et al. |
| 2012/0083727 A1 | 4/2012 | Barnett |
| 2012/0123533 A1 | 5/2012 | Shiuey |
| 2012/0157912 A1* | 6/2012 | Sorensen ................ A61M 1/77 604/35 |
| 2012/0172907 A1 | 7/2012 | Lee Shee et al. |
| 2012/0191120 A1 | 7/2012 | Linsi |
| 2012/0239056 A1 | 9/2012 | Dijkman et al. |
| 2013/0023918 A1 | 1/2013 | Morlet |

(56) References Cited

U.S. PATENT DOCUMENTS

| | | | |
|---|---|---|---|
| 2014/0030273 | A1 | 1/2014 | Verploegen et al. |
| 2014/0121697 | A1 | 5/2014 | Scheller et al. |
| 2014/0364885 | A1* | 12/2014 | Wells ................ A61F 9/00763 |
| | | | 606/170 |
| 2015/0045820 | A1 | 2/2015 | Kahook |
| 2015/0080896 | A1 | 3/2015 | To et al. |
| 2015/0112372 | A1 | 4/2015 | Perez Grossmann |
| 2016/0354248 | A1 | 12/2016 | Kahook |
| 2017/0181892 | A1 | 6/2017 | Kahook et al. |
| 2017/0367890 | A1 | 12/2017 | Kahook |
| 2018/0133056 | A1 | 5/2018 | Kahook |

FOREIGN PATENT DOCUMENTS

| | | |
|---|---|---|
| CN | 103025281 | 4/2013 |
| CN | 104758118 | 7/2015 |
| CN | 105792783 | 7/2016 |
| CN | 105899170 | 8/2016 |
| CN | 106029019 | 10/2016 |
| EP | 0 073 803 A1 | 3/1983 |
| EP | 1 455 698 A1 | 9/2004 |
| EP | 1 615 604 A1 | 1/2006 |
| EP | 2 303 203 A1 | 4/2011 |
| JP | S46-25677 Y1 | 9/1971 |
| JP | 2007-501687 | 2/2007 |
| JP | 2007-524472 | 8/2007 |
| JP | 2014-527424 | 10/2014 |
| KR | 10-2004-0058309 A | 7/2004 |
| KR | 10-2016-0040226 | 4/2016 |
| WO | 91/17793 A1 | 11/1991 |
| WO | 98/27876 A | 7/1998 |
| WO | 2001/078631 A2 | 10/2001 |
| WO | 02/056805 A2 | 7/2002 |
| WO | 2003/045290 A1 | 6/2003 |
| WO | 2004/093761 A1 | 11/2004 |
| WO | 2004/110501 A2 | 12/2004 |
| WO | 2009/140185 A1 | 11/2009 |
| WO | 2011/030081 A1 | 3/2011 |
| WO | 2012/044952 A2 | 4/2012 |
| WO | 2012/137186 A1 | 10/2012 |
| WO | 2013/163034 A1 | 10/2013 |
| WO | 2015/168176 | 11/2015 |
| WO | 2017/112893 A1 | 6/2017 |

OTHER PUBLICATIONS

Dominguez, A. "Ab Interno Trabeculotomy," Bulletins et Memoires de la Societe Francaise, vol. 86, 1973.
Esfandiari, et al. "Goniotome Trabecular Meshwork Excision: A cost-Conscious Solution to Ab Interno Trabeculectomy with Pristine Angle View", Ophthalmology Management, 2018.
Examination Report received for Indian Patent Application Serial No. 201947037130 dated Oct. 11, 2021, 6 pages.
Extended European Search Report dated Oct. 26, 2020 in the corraponding European patent application No. 18754639.5.
First Office Action received for Chinese Patent Application Serial No. 201880025455.5 dated Oct. 8, 2021, 14 pages (Including English Translation).
Francis, et al. "Ab Intemo Trabeculectomy: Development of a Novel Device (Trabectome) and Surgery for Open-Angle Glaucoma", Journal of Giauooma 15(1), 2006, pp. 68-73.
Grant, W. M. "Clinical Measurements of Aqueous Outflow", AMA Archives of Ophthalmology 46(2), 1951, pp. 113-131.
Grant, W. M. "Experimental Aqueous Perfusion in Enucleated Human Eyes", Archives of Ophthalmology, 69(6), 1963, pp. 783-801.
Herschler, et al. "Modified Goniotomy for Inflammatory Glaucoma. Histologic Evidence for the Mechanism of Pressure Reduction", Archives of Ophthalmology, 98(4), 1980, pp. 684-687.
Jacobi, et al. "Goniocurettage for Removing Trabecular Meshwork: Clinical Results of a New Surgical Technique in Advanced Chronic Open-Angle Glaucoma", American Journal of Ophthalmology, 127(5), 1999, pp. 505-510.
Jacobi, et al. "Technique of Goniocurettage: A Potential Treatment for Advanced Chronic Open Angle Glaucoma", British Journal of Ophthalmology, vol. 81, 1997, pp. 302-307.
Jea, et al. "Ab Interno Trabeculeclomy Versus Trabeculectomy for Open Angle Glaucoma," Ophthalmology 119(1), 2012, pp. 36-42.
Johnson, et al. "Human Tiabecular Meshwork Organ Culture. A New Method", Investigative Ophthalmology and Visual Science, 28(6), 1987, pp. 945-953.
Luntz, et al. "Trabeculotomy Ab Externo and Trabeculectomy in Congenital and Adult-Onset Glaucoma", American Journal of Ophthalmology, 83(2), 1977, pp. 174-179.
Minckler, et al. "Clinical Results with the Trabectome for Treatment of Open-Angle Glaucoma", Ophthalmology, 112(6), 2005, pp. 962-967.
Pantcheva, et al. "Ab Interno Trabeculectomy", Middle East African Journal of Ophthalmology, 17(4), 2010, pp. 287-289.
PCT International Search Report dated Jul. 10, 2018 in related PCT Application No. PCT/US2018/000018.
Quigley, et al. "The Number of People with Glaucoma Worldwide in 2010 and 2020", British Journal of Ophthalmology, 90(3), 2006, pp. 262-267.
Quintana, "Gonioscopic Trabeculotomy, First Results", Second European Glaucoma Symposium, Helsinki, 1984, pp. 265-271.
Search Report received for Chinese Patent Application No. 2018800254555, dated Sep. 16, 2021, 1 page.
Seibold, et al. "Preclinical Investigation of Ab Interno Trabeculectomy Using a Novel Dual-Blade Device", American Journal of Ophthalmology, 155(3), 2013, pp. 524-529-.e529.e2.
Skjaerpe, F., "Selective Trabeculectomy. A Repon of a New Surgical Method for Open Angle Glaucoma", ACTA Ophthalmologica, vol. 61, 1983, pp. 714-727.
Soohoo, et al. "Ab Interno Trabeculectomy in the Adult Patient", Middle East African Journal of Ophthalmology, vol. 2, No. 1, Jan.-Mar. 2015, pp. 25-29.
Tan, et al. "Postoperative Complications after Glaucoma Surgery for Primary Angle-Closure Glaucoma vs Primary Open-Angle Glaucoma", Archives of Ophthalmology, 129(8), 2011, pp. 987-992.
Ting, et al. "Ab Interno Trabeculectomy: Outcomes in Exfoliation Versus Primary Open-Angle Glaucoma", Journal of Cataract and Refractive Surgery, 38(2), 2012, pp. 315-323.
Office Action for EP Patent Application No. 18754639.5, dated Jun. 6 2023, 6 pages.

* cited by examiner

DEVICES, SYSTEMS AND METHODS FOR MINIMALLY INVASIVE GLAUCOMA SURGERY

RELATED APPLICATIONS

This patent application is a continuation of the U.S. patent application Ser. No. 15/932,355, filed Feb. 16, 2018, which claims priority to U.S. Provisional Patent Application No. 62/460,061, filed Feb. 16, 2017 and U.S. Provisional Patent Application No. 62/584,613, filed Nov. 10, 2017, the entire disclosure of each such application being expressly incorporated herein by reference.

FIELD OF THE INVENTION

The present invention relates generally to the fields of medicine and engineering and more particularly to surgical devices and methods for performing surgery.

BACKGROUND

Pursuant to 37 CFR 1.71(e), this patent document contains material which is subject to copyright protection and the owner of this patent document reserves all copyright rights whatsoever.

One surgical procedure used to treat certain types of glaucoma is a goniectomy. In a surgical goniectomy, a tissue cutting or ablating device is inserted into the anterior chamber of the eye and used to remove a full thickness strip of the tissue from the trabecular meshwork overlying Schlemm's canal. In many cases, a strip of about 2 mm to about 10 mm in length and about 50 µm to about 500 µm in width is removed. This creates a permanent opening in the trabecular meshwork through which aqueous humor may drain. The goniectomy procedure and certain prior art instruments useable to perform such procedure are described in U.S. patent application Ser. No. 10/052,473 published as No. 2002/0111608A1 (Baerveldt), the entirety of which is expressly incorporated herein by reference.

For opening of the trabecular meshwork (TM) to lower intraocular pressure (IOP) for treatment of the eye disease glaucoma, the procedure needs to remove a strip of the TM overlying Schlemm's canal. Furthermore, the distal or back wall of Schlemm's canal, with its ostia for drainage of aqueous humor from the eye via the collector channels, must be protected so that their efficacy is maintained.

If the device only makes a single cut (like a classical goniotomy knife used for surgical management of pediatric glaucoma), all of the TM tissue remains behind. For adults, the outcomes for such a procedure may be prone to having the access of fluid drainage via the collector channels in Schlemm's canal become blocked over time as this remnant tissue clogs such access for fluid outflow via the collector channels. Furthermore, if the back wall of Schlemm's canal and its outflow ostia are injured during the procedure, their drainage efficacy will most likely be compromised. A device that protects the back wall of Schlemm's canal while removing a strip of TM also greatly enhances the safety of such a procedure (i.e. providing a means for preventing cutting too deep and thus cutting into the back wall of Schlemm's canal.

In addition, such a device must be properly sized for ab-interno access through a small incision into the anterior chamber of the eye (typically a small corneal incision). Furthermore, the working end or distal tip of such a device must also be properly sized relative to the anatomy of Schlemm's canal, and it must be properly oriented with respect to the shaft that transverses between the incision point and the treatment zone of Schlemm's Canal in order to be functional.

There remains a need in the art for the development of new goniotomy devices and methods whereby a strip of TM tissue is removed to expose the ostia of collector channels in the lateral or outer wall of Schlemm's canal, thereby allowing aqueous humor to freely drain from the anterior chamber of the eye through those collector channels which in turn results in a lowering of intraocular pressure in the treated eye.

SUMMARY

In accordance with the present invention, there are provided devices and method useable for forming opening in the trabecular meshwork of eyes to facilitate drainage of aqueous humor and resultant lowering of intraocular pressure.

In accordance with one aspect of the present invention, there is provided a device which comprises a shaft and a distal member or foot on a distal end of the shaft. The distal member or foot may have a forward tip, a right edge, a left edge and a transversely concave depression, cavity or space between the right and left edges. The distal member is insertable into Schlemm's canal of an eye and thereafter advanceable through Schlemm's canal such that trabecular meshwork tissue will be cut by the right and left edges. In some embodiments, the edges may incline. In some embodiments, the edges may be non-parallel and may twist, rotate, curl or otherwise change in orientation as they progress rearwardly. In some embodiments, the device may optionally include lumens, opening or ports and associated connectors for infusing irrigation fluid and/or aspirating fluid and/or matter from the eye. In some embodiments, the width of the distal member and/or the width between the edges may become wider as it progresses rearwardly Further in accordance with the invention, the distal member may comprise a forward tip, right and left edges and wing members. The right and left edges extend over leading surfaces of the wing members.

Further in accordance with the invention, there are provided methods for using the devices of the present invention to form openings in trabecular meshwork tissue of mammalian eyes, as described herein.

Still further aspects and details of the present invention will be understood upon reading of the detailed description and examples set forth here below.

BRIEF DESCRIPTION OF THE DRAWINGS

The following detailed description and examples are provided for the purpose of non-exhaustively describing some, but not necessarily all, examples or embodiments of the invention, and shall not limit the scope of the invention in any way.

DETAILED DESCRIPTION

The following detailed description and the accompanying drawings to which it refers are intended to describe some, but not necessarily all, examples or embodiments of the invention. The described embodiments are to be considered in all respects only as illustrative and not restrictive. The contents of this detailed description and the accompanying drawings do not limit the scope of the invention in any way.

Described below and shown in the accompanying drawings are non-limiting examples of devices for manually cutting a strip of TM while avoiding damage to the back wall of Schlemm's canal. In these examples, the devices may be sized for ab interno access through a small incision into the anterior chamber of the eye (typically a small corneal incision). Furthermore, the working end or distal tip of each device may be sized relative to the anatomy of Schlemm's canal and properly oriented with respect to the shaft that transverses between the incision point and the treatment zone of Schlemm's Canal in order to be functional to remove a strip of TM tissue via an ab interno approach.

Removing a strip of TM tissue is critical to expose collector channels in the distal wall of Schlemm's canal to allow outflow of aqueous from the eye and lower intraocular pressure in glaucoma patients.

FIGS. 1 through 4B show one possible embodiment of a surgical handpiece device 10 according to the present invention. This handpiece 10 generally comprises a handle 30, a shaft 12 that extends distally from the handle 30 and a distal member 14 (which is alternatively referred to herein as a "foot") on the distal end of the shaft 12. In this example the distal member 14 has a bottom surface B, right and left upwardly extending side walls 22 and a cavity or open area 18 between the side walls 22 and rearward of the forward tip 16. The forward tip 16 may be tapered to a blunt point as shown. As explained in greater detail below, edges 20 form the sides of the forward tip 16 and transition in orientation as they progress in the rearward direction to form spaced-apart, upwardly-sloping top surfaces of the sidewalls 22. All or portions of the upwardly sloping regions of edges 20 may be sharpened, beveled, serrated, or otherwise configured to form cutting regions 21 which facilitate cutting of tissue as it advances over those edges 20. Also, the side walls 22 and/or edges 20 may be non-parallel such that the space 18 between the sidewalls 22 and/or edges 20 becomes wider as it progresses in the rearward direction. This optional widening or non-parallelism of the side walls 22 and/or edges 20 may serve to transverse stretch or transversely tighten tissue as it advances up the progressively-widening, upwardly-sloping regions of edges 20.

Optionally, the device 10 may include lumens, outlets and connectors for infusion of irrigation fluid into and/or aspiration of fluid/matter. In the example shown in FIGS. 1-4B, the shaft 12 comprises an inner tube 24 and an outer tube 26. The inner tube 24 extends out of and beyond the distal end of the outer tube 26, as shown. The inner tube 24 has a smaller outer diameter than an inner diameter of the outer tube 26 such that when inner tube 24 is positioned within the outer tube 26, for example, substantially coaxial therewith, the outer tube 14 inner surface is spaced apart from the inner tube 24 outer surface thereby defining an annular lumen which communicates with outlet port 28. The distal end of the outer tube 26 tapers down and is in sealing contact with the outer surface of the protruding inner tube 24, as shown. The opening 28 is positioned slightly above the location where the inner tube 24 exits the distal end of the outer tube 26.

Figure 2:
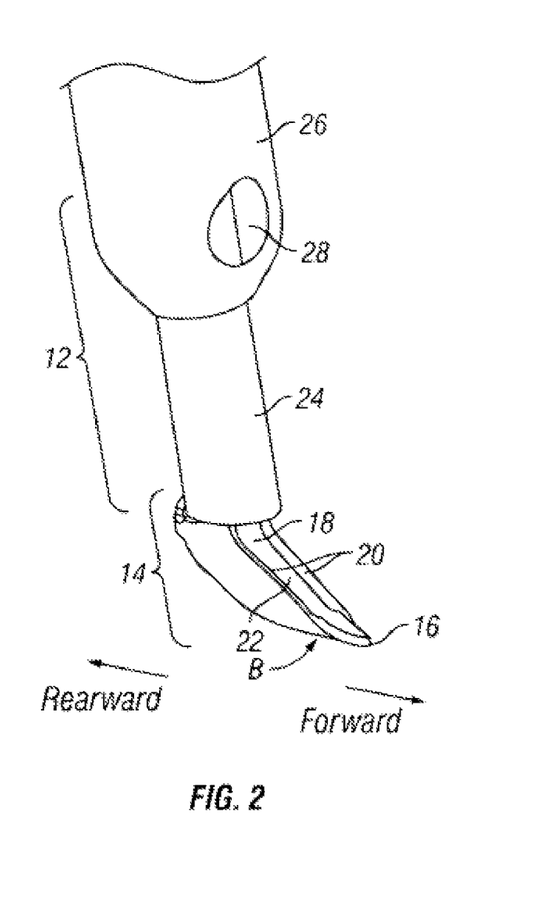
FIG. 2 is an enlarged view of a distal portion of the device of FIG. 1.

The inner tube 24 has an open distal end which is positioned immediately above the space 18 defined between the edges 20 and side walls 22. As seen in FIG. 2, embodiments which include the optional infusion and/or aspiration may also have tubular infusion and aspiration connectors 32, 34 for connecting sources of irrigation fluid and aspiration to the desired irrigation/aspiration lumens of the shaft 12.

More specifically, in the particular non-limiting example shown, tubular connector 32 is configured for connection to a source of irrigation fluid and communicates with the annular lumen that extends through the outer tube around the outer surface of the inner tube 24, thereby facilitating infusion of irrigation fluid through the outer tube 26 and out of opening 28. Tubular connector 34 is configured for connection to an aspiration pump or suction source to facilitate aspiration of fluid and or other matter from the space 18, into the open distal end of inner tube 24, through the lumen of inner tube 24 and out of tubular connector 34.

In many procedures it will be beneficial to have active irrigation (to pressurize and maintain the volume of the anterior chamber and to open access between the top of iris and the inner surface of the cornea to facilitate access to the TM) and active aspiration (to clear visualization of the treatment area from debris and blood reflux) during angle surgery procedures. Active irrigation also generally eliminates the need to inject viscoelastics into the angle during surgery, saving surgical costs as well as improving the surgical view of the TM (use of viscoelastics often distorts the view of the TM due to changes in refractive index between the viscoelastics and the irrigation fluid). However, if the device 10 includes the optional infusion/aspiration capability as described herein and the user does not wish to use irrigation or aspiration in a particular procedure, the user may optionally purge the air from the I/A channels and connect the irrigation and aspiration connectors 32, 34 together. Alternatively, in some embodiments, the I/A channels may be plugged or non-existent. In procedures where irrigation and aspiration are not used or unavailable, viscoelastic may be injected into the anterior chamber of the eye to maintain access to and visualization of the angle during the procedure.

In embodiments that are equipped with the optional irrigation/aspiration capability, aspiration flow rates of approximately 10-12 ml/min may be desirable to keep the field clear of reflux blood, stabilize TM during excision, and effect removal by aspiration of the cut strip of TM tissue without requiring use of an additional instrument (e.g., forceps) for the removal. Aspiration flow rates in the greater range of approximately 4-15 ml/min may also have some utility, and all aspiration flow rates>0 ml/min may be effective to at least clear reflux blood accumulation.

The bottom B of the distal member 14 is preferably smooth and atraumatic to the outer wall of Schlemm's Canal or to the collector channels that emanate from Schlemm's Canal when the distal member 14 is inserted in and advanced through Schlemm's Canal in the manner described herein. The distal member 14 in this non-limiting example is transversely concave or U-shaped, as may be appreciated from the FIG. 6, including the transverse cross sectional views of FIGS. 6A through 6D. However, it is to be understood that the distal member 14 may have other alternative shapes including trough-like shapes, V-shapes, or other shapes in which a transverse cavity or depression exists between edges 20. The bottom surface B of the distal member 14 is preferably smooth and/or otherwise configured such that it will not cause trauma or clinically significant damage to the outer wall of Schlemm's Canal as the distal member 14 is advanced through Schlemm's Canal as described herein. The forward tip 16 of the distal member 14 may be pointed or otherwise configured to easily pierce through the TM for entry of the tip and distal member into Schlemm's Canal. However, this tip 16 (including its edges) is preferably sufficiently blunt and/or atraumatic so as not to damage the distal wall of Schlemm's Canal or collector channels which emanate from Schlemm's Canal as the distal member 14 is advanced, tip 16 first, through the TM and into and while advanced along Schlemm's Canal. The tip 16 may also help to guide the distal member along the path of the lumen of Schlemm's Canal as the distal member is advanced through Schlemm's Canal.

In the non-limiting example shown, the upper surface of the distal member is generally trough-shaped (e.g., U-shaped), with the first and second inclined side walls 22 onto which are formed tissue-severing edges or blades 20. These edges 20 are spaced apart, as shown.

The open distal end of the inner tube 24 is positioned at the top of the cavity 18 that exists between the side walls 22 of the distal member 14 such that aspirated matter or a strip of tissue severed by the edges 20 travel through the elongate cavity 18 and into the open distal end of inner tube 24. Also, when both aspiration and irrigation are employed, such capabilities of the device 10 may enable the operator to maintain a stable, desired fluid pressure within the anterior chamber of the eye. In addition, flow from the irrigation to the aspiration port of the device serves to maintain visualization of the treatment area by actively removing any tissue debris and/or blood reflux typically associated with collector channel exposure to the anterior chamber during such angle procedures.

Figure 7:
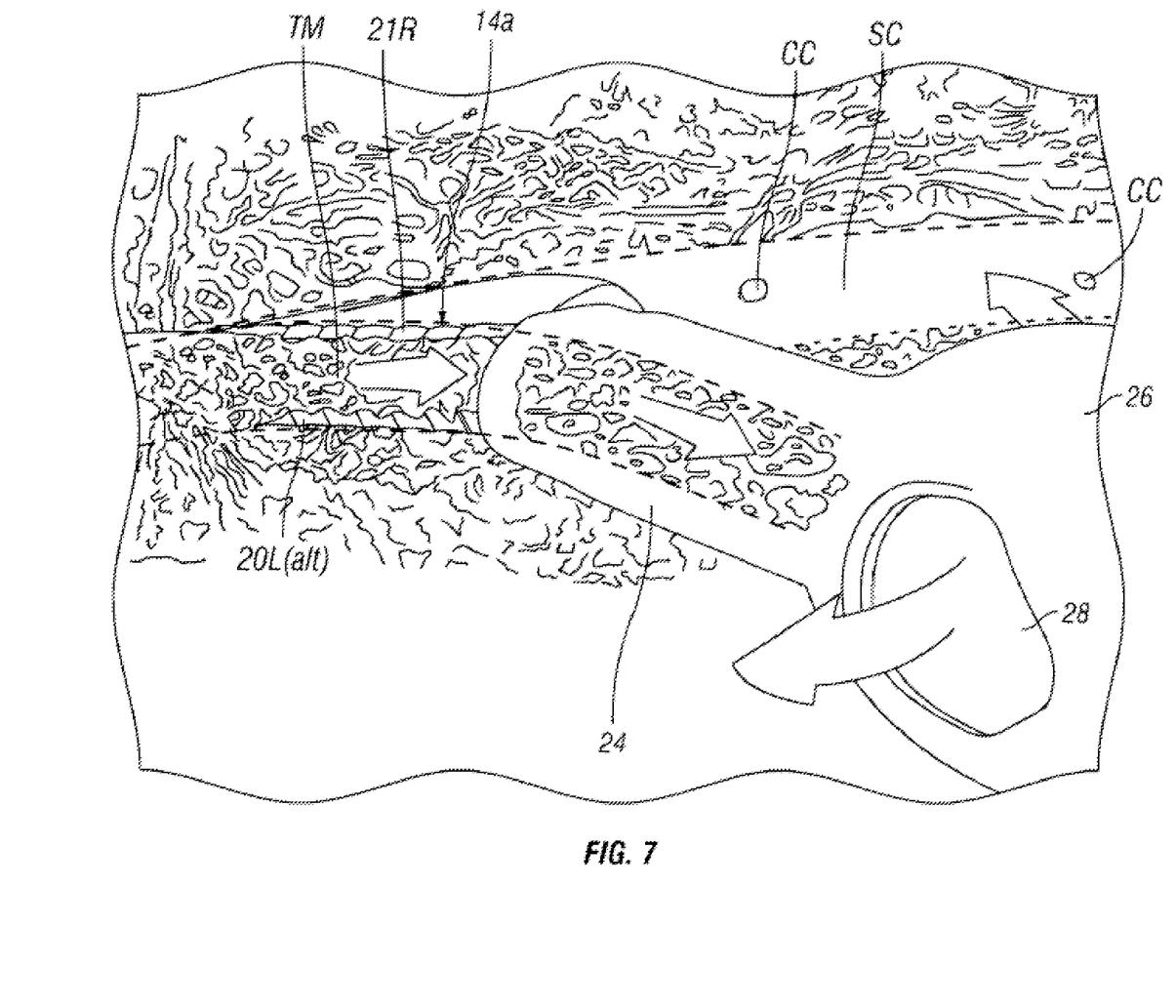
FIG. 7 is a diagram showing the device of FIGS. 5-6 being used to form an opening in TM tissue in a human eye in accordance with a method of the present invention.
Figure 8:
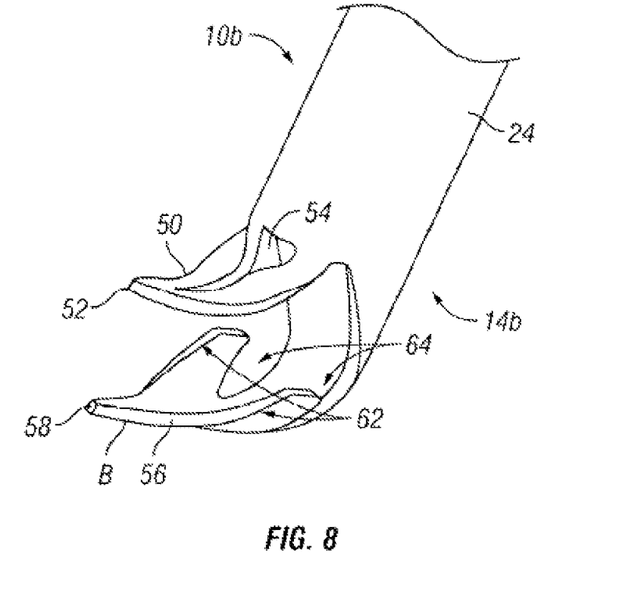
FIG. 8 shows a distal portion of another embodiment of a surgical hand piece device of the present invention.
Figure 8A:
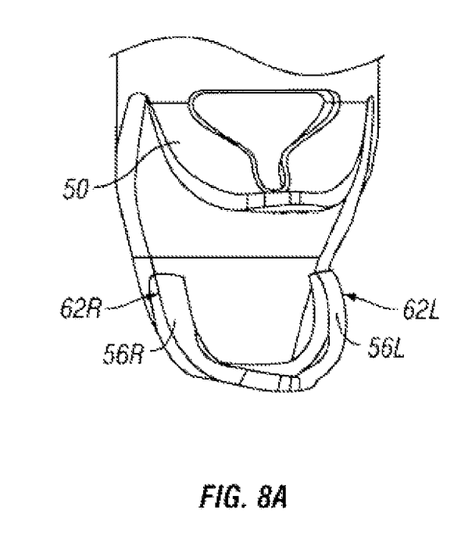
FIG. 8A is a partial enlarged view of the device of FIG. 8.
Figure 8B:
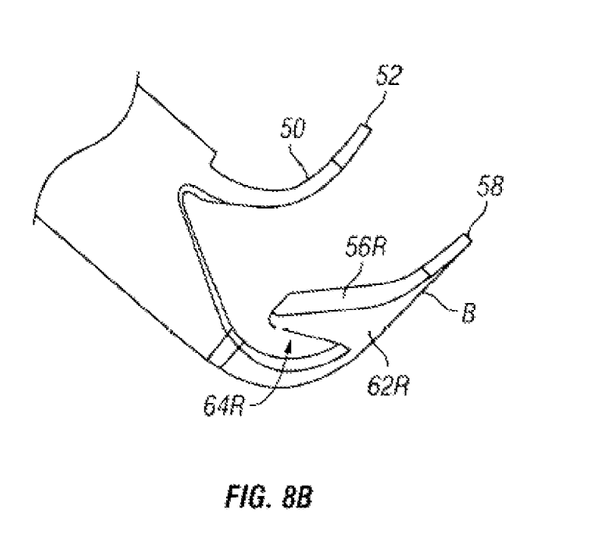
FIG. 8B is a partial left side view of the device of FIG. 8.
Figure 11:
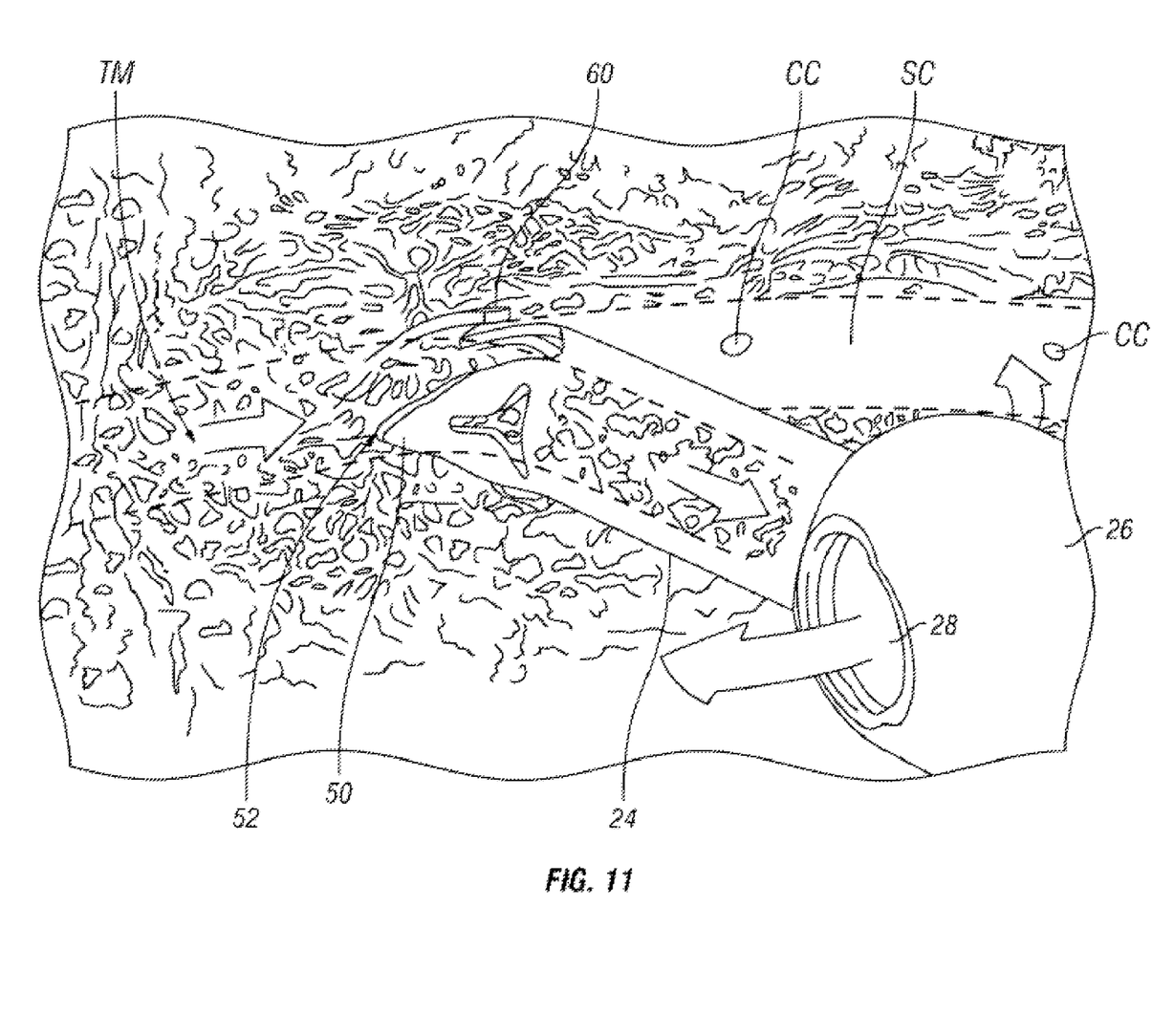
FIG. 11 is another diagram showing the device of FIGS. 5-6 being used to form an opening in TM tissue in a human eye in accordance with a method of the present invention.

When provided as a sterile disposable, the general surgical steps for use of the embodiment shown in FIG. 1 above, either with or without active I/A during the surgical procedure, are described in detail as follows:

First Option: Use With Ophthalmic I/A System:

1. Inspect all packages prior to use. Do not use if package is open or damaged.
2. Remove the Handpiece from its package in the sterile field.
3. Connect the irrigation connector 32 of the Handpiece to the irrigation line connector of the I/A system's fluidics set. Connect the aspiration connector of the Handpiece 34 to the aspiration line connector of the I/A system's fluidics set. Place the Handpiece inclined tip down (with the purge chamber in place).
4. Activate I/A system's irrigation and aspiration, and purge the fluid lines until all bubbles are removed in both the Handpiece and I/A system's irrigation and aspiration lines. Turn off the I/A system's irrigation and aspiration.
5. Perform a clear corneal incision using surgical knife. Allowing the anterior chamber to de-pressurize facilitates blood congesting into Schlemm's canal, helping identify the location of the TM.
6. Carefully remove the purge chamber/clear cap 36 from the device 10 so the shaft 14 member does not touch the purge chamber.
7. The raised indicators 30 on the handpiece device 10 correspond to, and are a guide to, the rotational orientation of the distal member 14 and should be held perpendicular to the corneal incision.
8. Activate irrigation of the I/A system. Insert the shaft 12 of the handpiece device 10 through the corneal incision and into the anterior chamber of the patient's eye. The anterior chamber should deepen when the irrigation opening 28 of the handpiece device 10 clears the corneal incision and irrigation fluid begins to flow into the anterior chamber.
9. Advance the distal member 14 toward the TM opposite of the incision site. Establish gonioscopic view of the TM and proceed with advancing the member until it's smooth bottom surface B contacts the TM.
10. Pierce the TM with the pointed forward tip 16 so the distal member 14 enters Schlemm's Canal while avoiding damage to the back wall.
11. Activate aspiration of the I/A system (keeping irrigation also activated). The distal member 14 is then advanced along Schlemm's Canal in the direction intended to sever TM. Examples of this are shown in FIGS. 7 and 11 and are discussed more fully below. The smooth bottom surface B of the distal member 14 should exert only minimal pressure against the back wall of Schlemm's canal as the distal member 14 is advanced in the forward direction through Schlemm's canal.
12. As TM is excised, blood reflux or hyphema from collector channels may appear. The irrigation/aspiration components of the device 10 may be used to flush any such blood or other debris from the anterior chamber thereby improving or maintaining clear visualization of the treatment area.
13. Once a strip of TM tissue has been severed and detached, if it is not fully removed by aspiration through the inner tube 24 as described above, micro-forceps can be used to manually grasp and remove such tissue in accordance with operative techniques known in the field of Ophthalmology.
14. Gently remove the shaft 12 and distal member 14 from the corneal incision following the same orientation procedure using the raised indicators 30 as used during insertion.

15. At the end of the procedure, it is recommended to thoroughly remove any viscoelastic that may have been used, using standard I/A practice to avoid post-operative pressure spikes.

Second Option: Use Without Ophthalmic I/A System:
1. Inspect all packages prior to use. Do not use if package is open or damaged.
2. Remove the handpiece device 10 from its package in the sterile field.
3. It is important to remove air from the Handpiece and its I/A pathways to avoid air bubbles entering the anterior chamber. Connect the irrigation tubing connector 32 to a syringe containing BSS. In some embodiments, the irrigation connector 32 and/or aspiration connector 34 may be marked or color coded to easily distinguish one from the other. Place the handpiece device 10 with the shaft 12 inclined tip down (with the purge chamber/clear cap 36 in place) and hold purge chamber/clear cap 36 in place. Infuse BSS until the BSS exits the aspiration connector 34. Remove the syringe and connect the irrigation connector 32 and the aspiration connector 34 together. The irrigation and aspiration connectors may be configured (e.g., male Luer and female Luer) so as to directly connect to one another in this manner.
4. Perform a clear corneal incision using surgical knife.
5. Inject a viscoelastic into the anterior chamber to inflate and maintain its volume during the procedure. The volume of anterior chamber must be re-established and maintained per this step for continuing the procedure.
7. Carefully remove the purge chamber/clear cap 36 from the device 10 so the shaft 12 member does not touch the purge chamber.
8. The raised indicators 30 on the handpiece device 10 correspond to, and are a guide to, the rotational orientation of the distal member 14 and should be held perpendicular to the corneal incision.
9. Insert the shaft 12 and distal member 14 through the corneal incision and into the anterior chamber of the patient's eye.
10. Advance the distal member 14 toward the TM opposite of the incision site. Establish gonioscopic view of the TM and proceed with advancing the member until it's smooth bottom surface B contacts the TM.
11. Pierce the TM with the pointed forward tip 16 so the distal member 14 enters Schlemm's Canal while avoiding damage to the back wall.
12. The distal member 14 is then advanced along Schlemm's Canal in the direction intended to sever TM. Examples of this are shown in FIGS. 7 and 11 and are discussed more fully below. The smooth bottom surface B of the distal member 14 should exert only minimal pressure against the back wall of Schlemm's canal as the distal member 14 is advanced in the forward direction through Schlemm's canal.
13. As TM is excised, blood reflux or hyphema from collector channels may appear. Viscoelastic and/or BSS may be used to improve visualization in accordance with operative techniques known in the field of Ophthalmology.
14. Once a strip of TM tissue has been severed and detached, micro-forceps can be used to manually grasp and remove such tissue in accordance with operative techniques known in the field of Ophthalmology.
14. Gently remove the shaft 12 and distal member 14 from the corneal incision following the same orientation procedure using the raised indicators 30 as used during insertion.
15. At the end of the procedure, it is recommended to thoroughly remove any viscoelastic that may have been used, using standard I/A practice to avoid post-operative pressure spikes.

Figure 1:
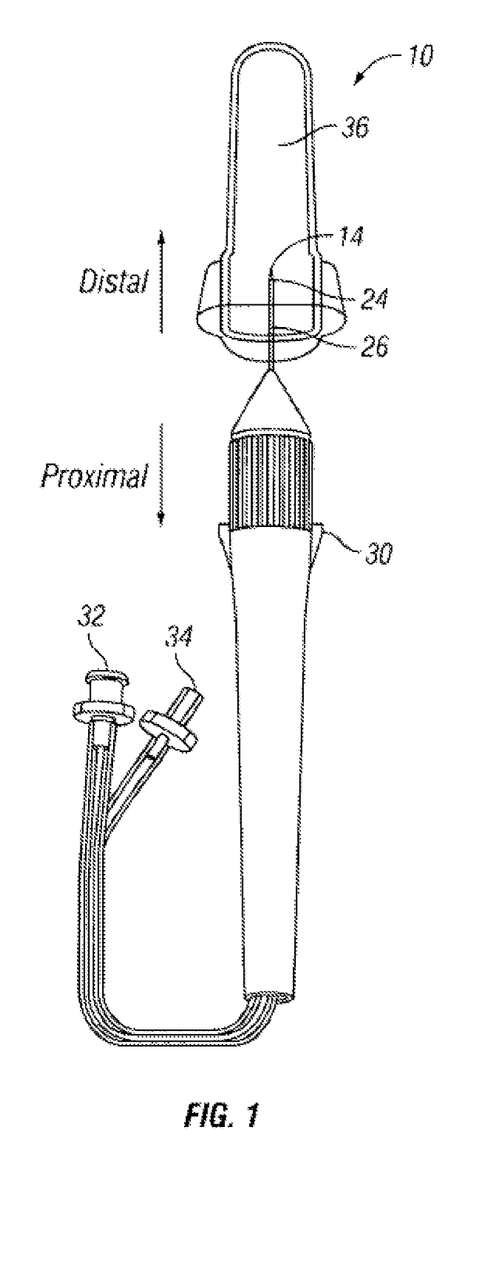
FIG. 1 shows one embodiment of a surgical hand piece device of the present invention.

When performing the surgical procedure without active irrigation and aspiration, it can be appreciated that the device 10 depicted in FIG. 1 could alternatively be provided without irrigation connector 32 and associated tubing to the handpiece, as well as being provided without aspiration connector 34 and associated tubing to the handpiece. In addition, device 10 could also alternatively be provided such that the outer irrigation tube 26 does not have an irrigation opening 28. For this alternative of device 10, the surgical procedure described under SECOND OPTION above can be performed without performing Step 3, thus facilitating ease of use and reducing surgical time.

For insertion of the device 10 the incision into the anterior chamber may be approximately 180 degrees (e.g., about diametrically opposite) from the sector of Schlemm's canal from which the operator intends to cut TM tissue. Such location of the incision allows for the shaft 12 and distal member 14 to be advanced centrally across the anterior chamber of the eye to the treatment sector of the angle that is about 180 opposite the incision (for example, if the incision is temporal, the treatment sector is nasal—the most commonly employed surgical approach).

Using this approach, it is important that the forward tip 16 of the distal member 14 be in the proper orientation relative to the shaft 12 to allow for piercing of the TM by the forward tip 16 as well as facilitating the ability to advance the distal member 14 of the device 10 into and along Schlemm's canal. In addition, this arrangement can provide for removal of TM from the desired treatment sector by advancing the distal member 14 through Schlemm's canal first in one direction (e.g., clockwise) and then in the other direction (e.g., counter-clockwise).

Figures 3, 3A:
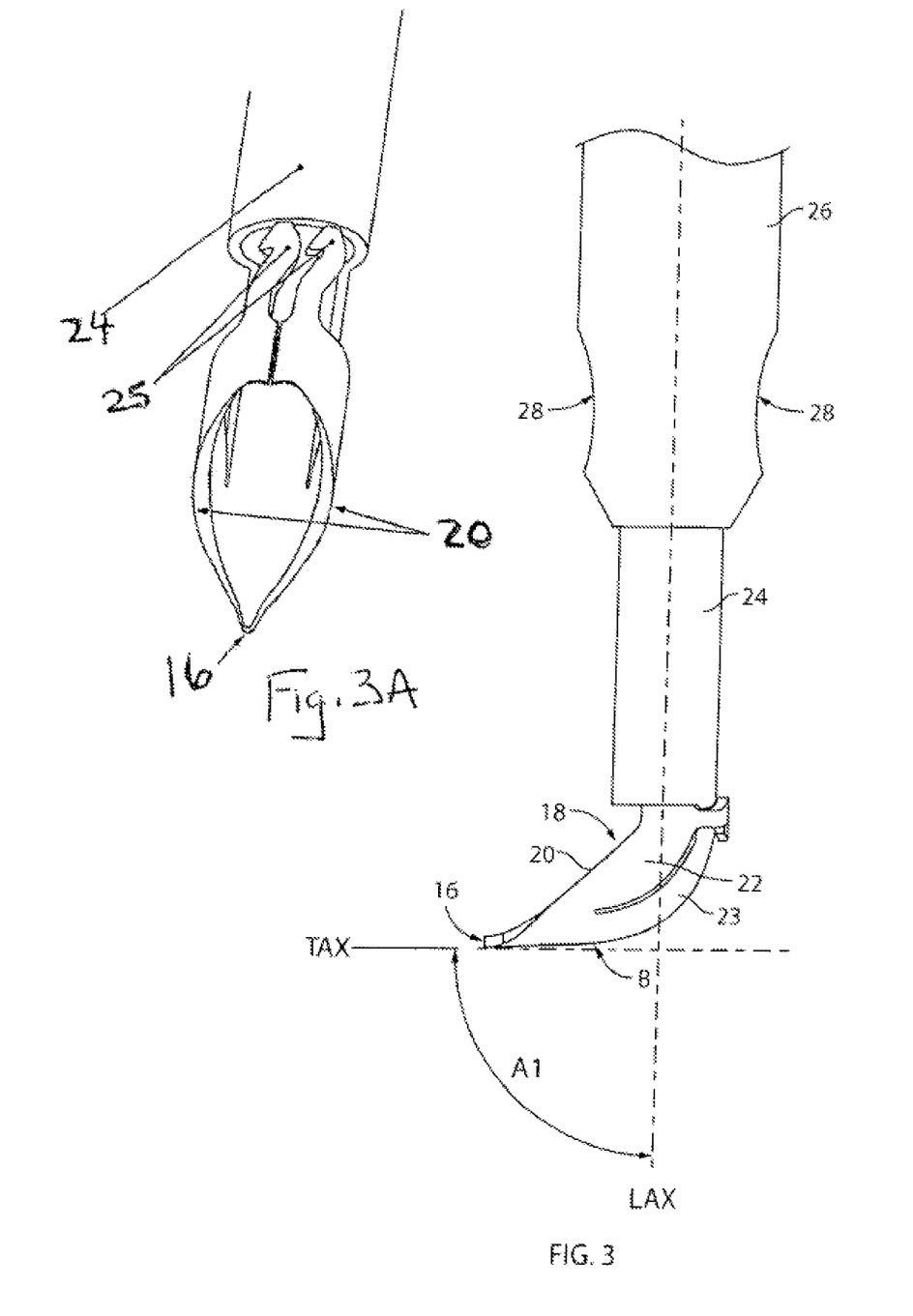
FIG. 3 is a side view of a distal potion of the device of FIG. 1.
FIG. 3A shows a work piece cut to form the distal member of the device of FIG. 1.

As labeled in FIG. 3, a longitudinal axis LAX is projectable through the shaft 12. A linear transverse axis TAX is projectable tangentially to the bottom surface B at the forward tip 16, as shown. The angle A1 between longitudinal axis LAX and transverse axis TAX may be about 85 degrees for optimal surgical utility. This allows one single device to perform both clockwise and counter-clockwise TM removal relative to the incision entry point into the anterior chamber. If angle A1 ranges between about 70 to 100 degrees good clinical utility will typically result in most eyes. However, so long as angle A1 is from about 30 degrees to about 120 degrees, some clinical utility would be maintained.

If there is curvature to or compound angling of the shaft 12 or any portion of the device 10 that inserts into the eye, then the angle perpendicular to the incision site relative to the angle of the distal member 14 at the treatment site may desirably be approximately 90 degrees (despite intervening angling or curvature), with clinical utility if this angle ranges from about 30 degrees to about 120 degrees.

With respect to proper sizing, it is desirable for the shaft 12 and distal member to be insertable through a minimal incision size. It can be appreciated that the current invention can be designed without irrigation and aspiration, potentially using a solid probe shaft and/or by other means. However, with inclusion of I/A capability, this may limit insertion size through about a 1.8 mm incision for sufficient inflow and outflow. However, the device would still have clinical utility if insertable through an incision of less than 2.8 mm (since such incision sizes are commonly used for cataract removal surgery).

Also with respect to proper sizing, it can be appreciated that the device will be guided down Schlemm's canal when severing a strip of TM. In its natural state, the basic lumen width of Schlemm's Canal is approximately 350 microns, or about 0.014 inches. In addition, the canal lumen is noncircular and basically collapsed in height (often described as about approximately 25-50 microns, or 0.001-0.002 inches).

For proper sizing of the member features of the device, it can be appreciated that the TM forming the front wall of Schlemm's Canal demonstrates a high degree of elasticity, and the scleral back wall of Schlemm's canal is much less elastic but deformable. These factors need to be considered for sizing features of the tip of the device since the pointed tip will be used to gain entry into and help guide the member down the lumen of Schlemm's canal as it is advanced.

An important sizing factor is the general width of the member in the direction it is advanced along Schlemm's canal. Although the TM is elastic, the tip of the member must be insertable into the lumen of Schlemm's canal and must be advanceable, together with the portion of the member that lies between the tip and the point at which the tissue-severing blades on the inclined side edges cause the TM to sever as it is advanced.

Figure 4:
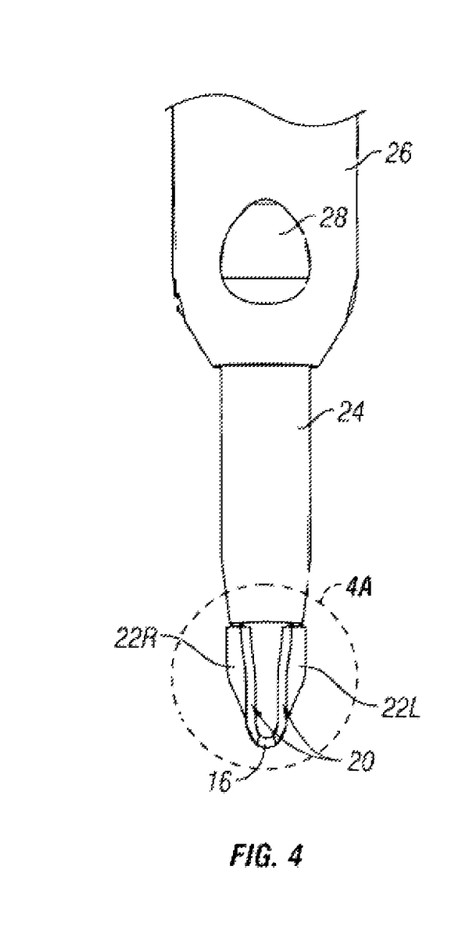
FIG. 4 is a front view of a distal portion of the device of FIG. 1.

FIG. 4 shows front and side views of the tip of the device

Figure 4A:
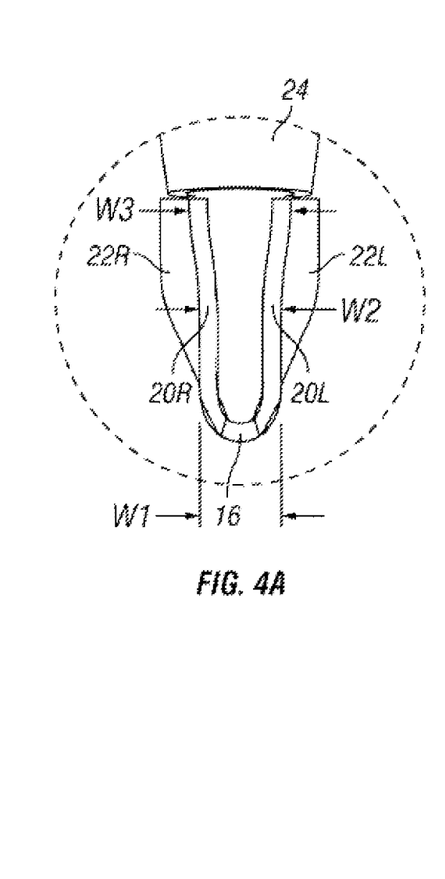
FIG. 4A is an enlarged view of portion 4A of FIG. 4.
Figure 4B:
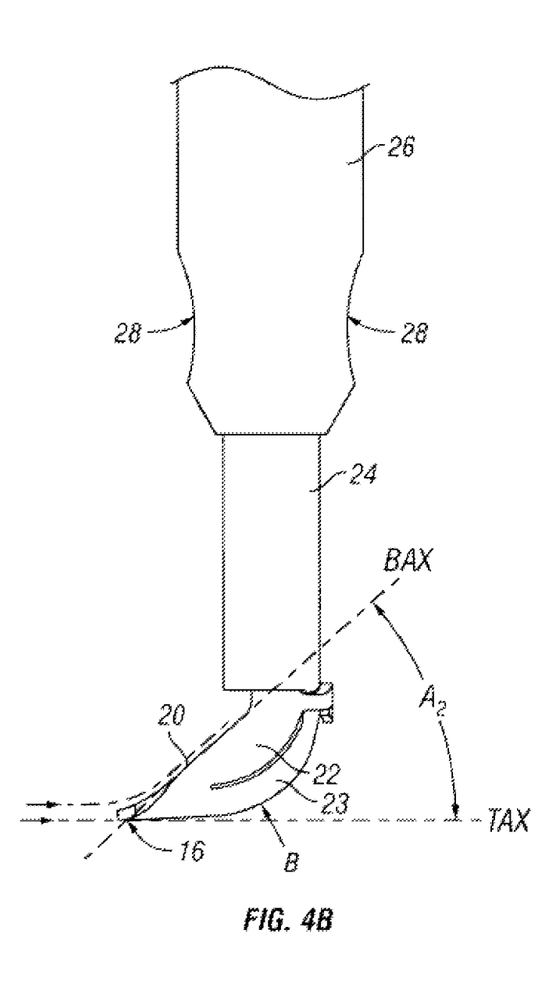
FIG. 4B is a side view of FIG. 4 labeled to indicate a blade axis (BAX) over which TM tissue advances in accordance with one method of the present invention.

With reference to the showing of FIGS. 4, 4A and 4B, the forward-most portion of the distal member 14 may have a first width W1. Width W1 may be about 230 microns (0.009 inches). For good clinical utility, given the elasticity and deformity of Schlemm's canal, this width W1 may vary between about 150-300 microns (0.006-0.012 inches), and some clinical utility is likely maintained between 50-500 microns (0.002-0.020 inches).

When the forward tip 16 pierces the TM and the distal member 14 is advanced into Schlemm's Canal, the back wall of Schlemm's canal will be juxtaposed to the bottom surface B. As the distal member 14 advances through Schlemm's canal, the TM tissue will ride over and advance up the inclined portions of edges 20 and edges 20 will thereby cut a strip of TM tissue.

With specific reference to FIG. 4B, as the distal member 14 advances through Schlemm's canal, TM tissue will ride over the edges 20 generally along axis BAX as the edges incline. The angle A2 shown between transverse axis TAX and axis BAX depends on the angle of incline of each edge 20. The right edge 20R and left edge 20L may incline at the same or different angles A2. In the particular non-limiting example shown, both edges 20 incline at the same angle A2, which is preferably about 35 to 40 degrees as shown in FIG. 3, as this will place the TM under tension over a reasonably short distance along path 20 of the member so that the length of the member can remain compact. However, it is reasonable to assume that angle A2 could provide good clinical utility over the range of about 30 to 50 degrees, and maintain some clinical utility over a range between about 20 to 70 degrees.

Figure 5:
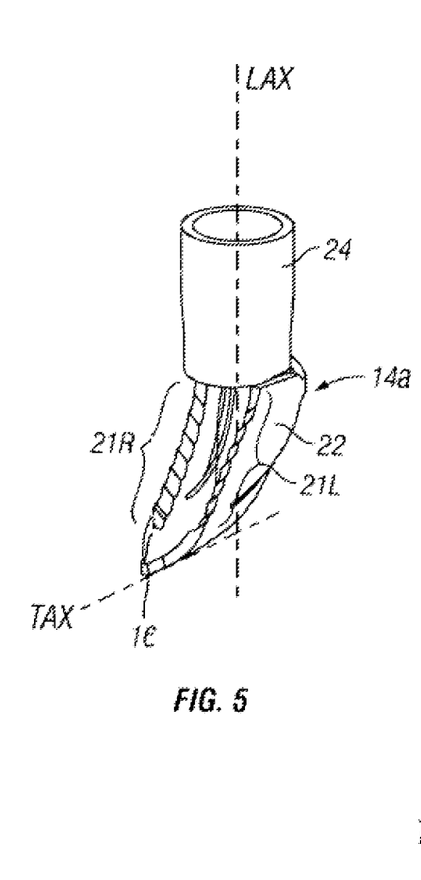
FIG. 5 shows a distal portion of the device of FIG. 1 modified to include optional serrated regions.
Figure 6:
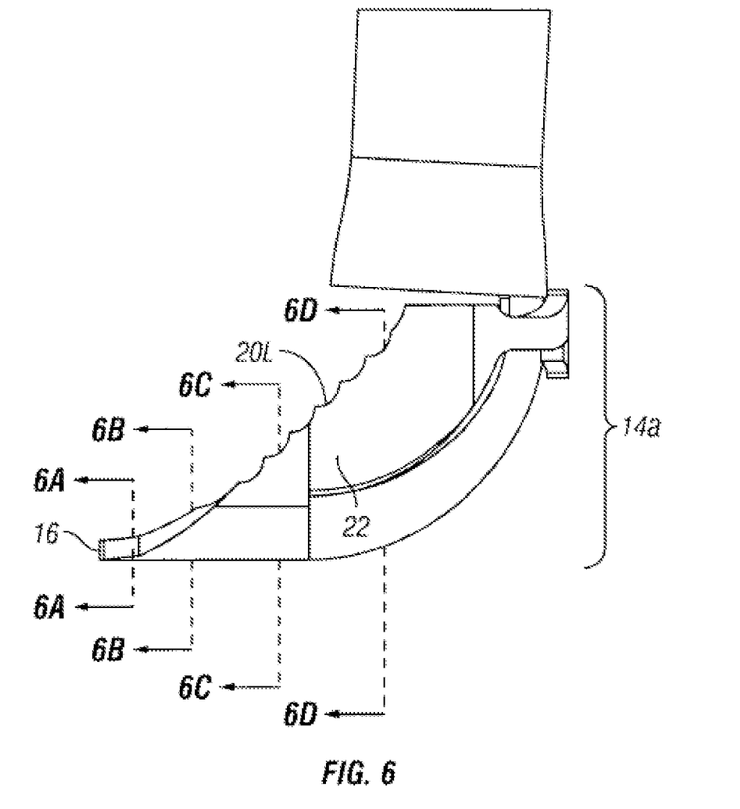
FIG. 6 is a side view of the distal portion of shown in FIG. 5.
Figure 6A:
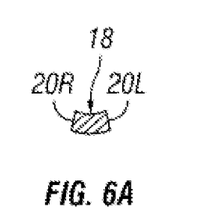
FIG. 6A is a transverse cross sectional view through Line 6A-6A of FIG. 6.
Figure 6B:
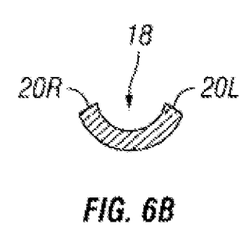
FIG. 6B is a transverse cross sectional view through Line 6B-6B of FIG. 6.
Figures 6C, 6D:
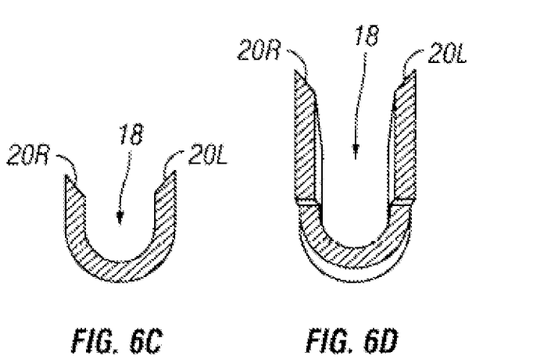
FIG. 6C is a transverse cross sectional view through Line 6C-6C of FIG. 6.
FIG. 6D is a transverse cross sectional view through Line 6D-6D of FIG. 6.

As TM tissue advances over the edges 20, the incline of the edges will cause the TM tissue to be lifted away from the back wall of Schlemm's canal. At the same time, in embodiments where the width between the edges (e.g., W1, W2, W3) becomes wider, such widening may also transversely pull or stretch the TM tissue as it advanced over edges 20. This separation between the TM and the back wall of Schlemm's Canal, as well as transverse widening between edges in embodiments where the width between the edges becomes wider, stretches the TM as it advances over the top surface of the tip and up the inclined tissue-severing blades 20, causing the TM to be opened by the two tissue-severing blades 20, thus creating a strip of TM. In embodiments where the tissue-severing blades 20 are generally separated by a distance W2, the strip of TM being severed by the blades will be roughly the width of W2, the distance between the tissue-severing blades 20. However, the actual width of the excised TM strip will vary from W2 due to the effects of the TM being stretched during excision. As shown in FIGS. 5 through 6D, some embodiments of the device 10 may have a distal member 14a whereon the edges 20 have regions 21 which are sharpened, beveled, serrated, stepped, roughened, or otherwise configured to enhance or facilitate cutting of the TM tissue. In the non-limiting example shown, these regions 21R, 21L are of serrated configuration and are formed on the inclined portions of both edges 20R and 20L. It is to be appreciated that in some embodiments and/or for some applications such region(s) 21 may be present on only one of the edges 20R or 20L and/or regions 21 of differing configuration may be present on the opposite edges.

Figure 5A:
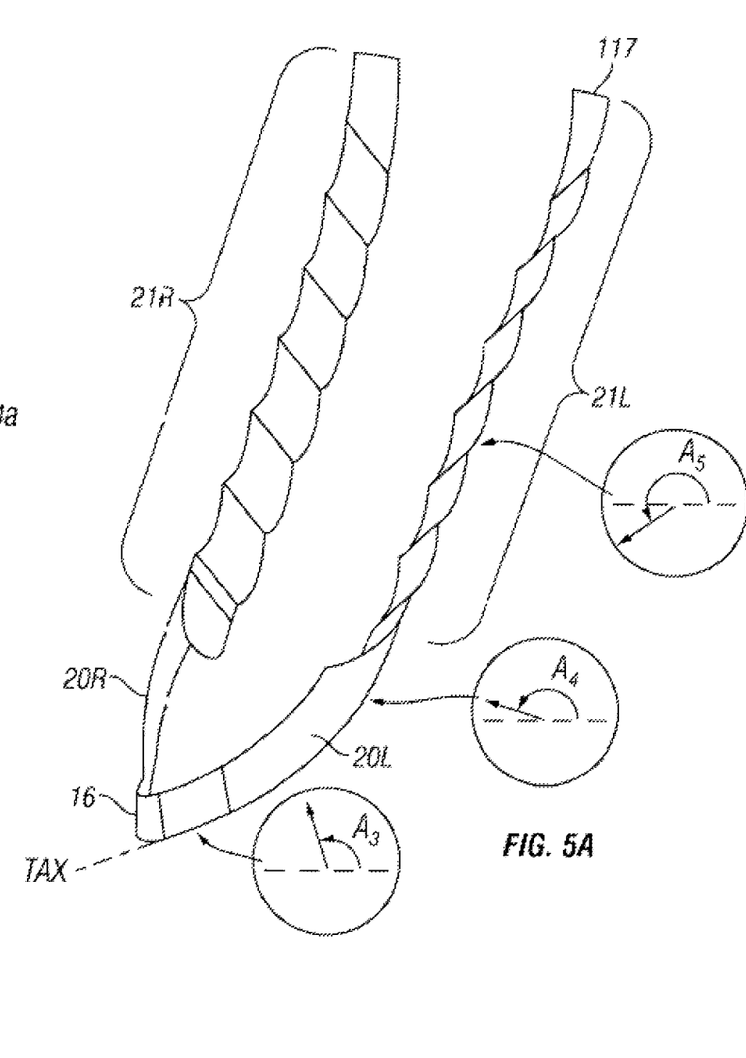
FIG. 5A is an enlarged, schematic diagram of edges of the device of FIG. 5 with plane of orientation indications shown at three locations along the left edge.

Also, as may be appreciated particularly from the showings of FIGS. 5A and 6A through 6D, in the example shown, the edges 20R, 20L may be non-planar and may rotate or curl as they progress in the rearward direction. FIG. 5A shows only the edges 20 of the device of FIG. 5, without the adjacent structures. FIGS. 6A through 6D show transverse cross-sectional views through spaced-apart locations A-A, B-B, C-C and D-D of FIG. 6. From these views, one can readily appreciate that, in this example, the edges are non-parallel and actually rotate or curl as they progress in the rearward direction. At a location near the forward tip 16 the edges may be vertical or nearly vertical and converge at the forward end to form a pointed or blunt point on the forward tip 16 that is capable of penetrating through TM tissue, as explained above. As labeled on FIG. 5A, an angle A3 is defined between each edge 20 and a horizontal transverse plane. As the edges 20 progress rearward, they progressively increase in height and rotate inwardly, as shown the cross-sectional views of FIGS. 6B and 6C. As labeled on FIG. 5A, at a location reward of angle A3 (e.g., at a point where the edges 20 begin to incline) the edges 20 are at an angle A4 relative to horizontal, such angle A4 being greater than angle A3. As the edges progress further rearward, they further rotate or curl to attitudes in past horizontal as seen in the cross-section of FIG. 6D. As labeled on FIG. 5A, at a location reward of angle A4 (e.g., at a point about midway up the inclined portions of edges 20) are disposed at an angle A5 relative to horizontal, such angle A5 being greater than angle A4 and, in this example, greater than 180 degrees.

The entire foot or distal member 14 may be formed of metal or other suitable material of a constant thickness. In particular, the thickness of the wall that forms the bottom B of the distal member 14 may remain constant, non-increasing and devoid of any upward sloped or planar ramp in the region that extends rearward from the front or distal tip 16 to the back or proximal side of the foot or distal member 14. In use, as shown in FIG. 7, as the distal member 14 advances through Schlemm's canal, TM tissue will ride over the non-planar, progressively rotating edges 20 and will bridge or be suspended across the open cavity 18 until the edges 20 (with or without optional cutting surfaces 21) have formed cuts or severances in the TM tissue. The resultant strip of laterally cut or severed TM tissue may then be aspirated from cavity 18 into the open distal end of tube 24, in embodiments which utilize aspiration.

The described member of the device can be fabricated by cutting a tube with the proper pattern that allows for subsequent formation of the tip features.

As illustrated in FIG. 3A, the distal member 14 of the device 10 may be manufactured by cutting (e.g., laser cutting) and then bending a distal portion of tube 24 such that the desired features of the distal member 14 are formed. As part of this cutting of the tube 24, the tissue-severing edges 20 with or without cutting surfaces 21 can be formed concurrently with the cutting or by secondary processing relative to cutting of the tube (either before or after forming of the member from the cut tubing).

When the tip is formed, the support members 25 may be formed and interconnected as seen in FIG. 3 to reinforce the strength of the distal member 14 in its formed configuration. It can be appreciated that there are many alternate cut patterns for the tube, inclusive or exclusive of features such as the support members, or any particular configurations thereof, that can be used to cut and form the member features of the current device.

The invention described to this point indicates an example of a preferred configuration and its sizing and orientation preferences and ranges. There are additional variations offering functional utility that are part of this disclosure.

FIGS. 8 through 11 show another embodiment of the device 10b. In this embodiment, the device 10b may be of the same construction as described above with respect to the first embodiment 10A, except that this device 10b has a different distal member 14b. In this device 10b, the distal member 14b has a bottom B, forward tip 58, edges 56 and winged members 62 with open areas 64 located rearward of the wing members 62.

Optionally, this device 10b (or any other device of this invention including the first embodiment 10) may include a pointer 50 positioned above the wing member 62. The pointer 50 may have a tip 52 which is directly aligned with the forward tip 58. As may be appreciated from FIG. 11, during use, the pointer 60 remains above the TM tissue so as to be readily visible to the operating surgeon even though the forward tip 58 and parts of the wing members 62 may be obscured because they are beneath the TM tissue. The surgeon may then use the pointed 50 to confirm the exact direction in which the forward tip 58 is advancing through Schlemm's canal.

The edges 56 form inclined tissue cutting surfaces on the fronts of the wing members 62. Optionally, as seen in FIG. 10, a modified distal member 14c may include areas or regions of edges 56 which are sharpened, beveled, serrated, or otherwise configured to form cutting regions 62 (alt) which facilitate cutting of tissue as it advances thereover.

Figures 9, 10:
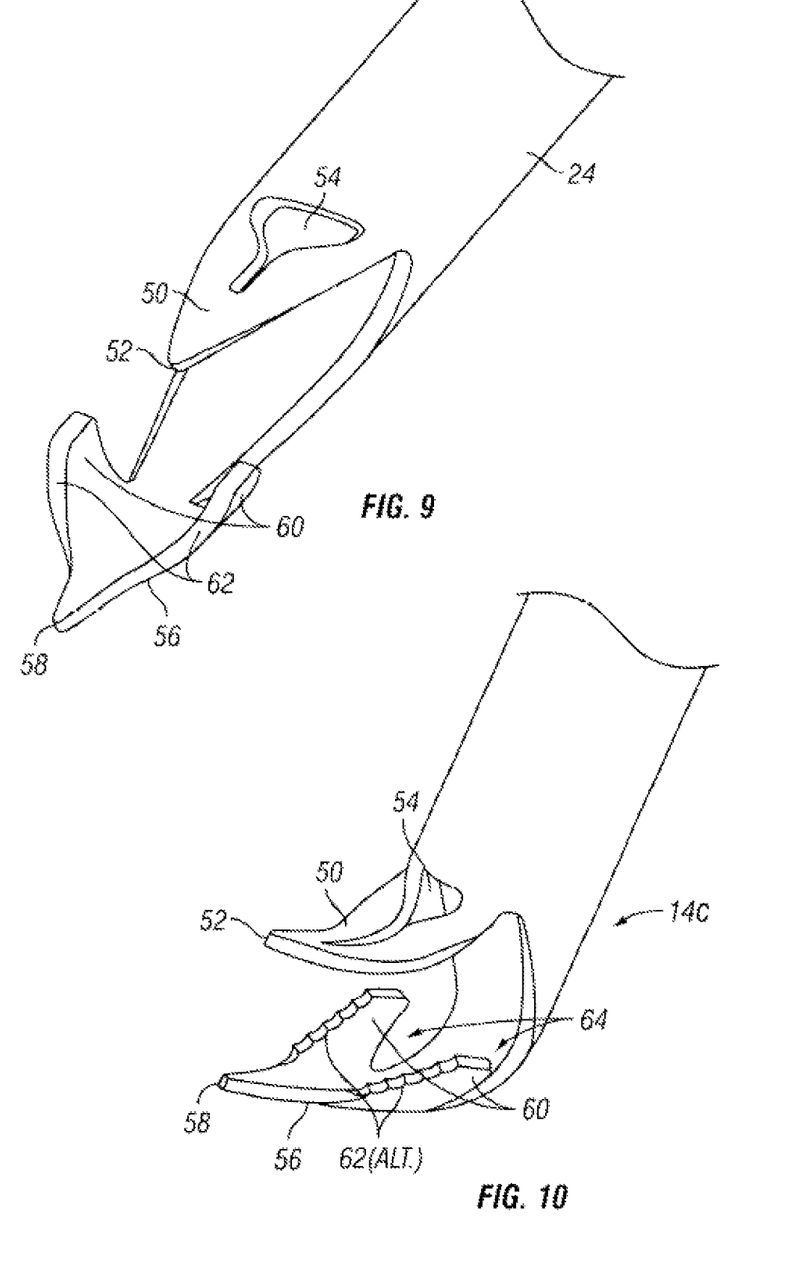
FIG. 9 shows a workpiece cut from tubular stock useable to form a distal portion of the device of FIG. 8.
FIG. 10 shows a distal portion of the device of FIG. 8 modified to include optional serrated regions.

It can be appreciated that such a tip configuration can be formed from a tubular structure using a cutting pattern as shown in FIG. 9. As illustrated in FIG. 9, a distal portion of the tube 24 is cut such that the features of the distal member 14b can be formed. As part of this cutting of the tube 24, optional tissue cutting regions or surfaces 62(alt) may be formed on the wing members 62 as shown in FIG. 10, and/or such tissue-severing blades may be formed by secondary processing relative to cutting of the tube (either before or after forming of the tip from the cut tubing).

Depicted in FIG. 11 is an illustration of the device having a distal member 14b with winged members 62 and pointer 50 being advanced through Schlemm's canal. As illustrated in FIG. 11, the optional pointer 50 provides a visual indicator of the direction of the underlying tip as it is advanced along Schlemm's Canal. Arrows in FIG. 11 show superimposed irrigation and aspiration flows. The manner in which the optional pointer 50 is constructed in this non-limiting example is merely one example of the ways in which the optional pointer may be constructed and it is intended to include all alternative constructions of pointers or direction indicators in this disclosure.

In an ab interno procedure to form an opening in the TM of an eye, the forward tip 58 may be inserted through the TM and into Schlemm's Canal beneath the TM with the pointer 50 remaining above the TM. The foot or distal member 14b or 14c is then advanced through Schlemm's Canal with the TM tissue being severed by edges 56R and 56L on the forward aspects of wing members 62.

It is to be appreciated that, although the invention has been described hereabove with reference to certain examples or embodiments of the invention, various additions, deletions, alterations and modifications may be made to those described examples and embodiments without departing from the intended spirit and scope of the invention. For example, any elements, steps, members, components, compositions, reactants, parts or portions of one embodiment or example may be incorporated into or used with another embodiment or example, unless otherwise specified or unless doing so would render that embodiment or example unsuitable for its intended use. Also, where the steps of a method or process have been described or listed in a particular order, the order of such steps may be changed unless otherwise specified or unless doing so would render the method or process unsuitable for its intended purpose. Additionally, the elements, steps, members, components, compositions, reactants, parts or portions of any invention or example described herein may optionally exist or be utilized in the absence or substantial absence of any other element, step, member, component, composition, reactant, part or portion unless otherwise noted. All reasonable additions, deletions, modifications and alterations are to be considered equivalents of the described examples and embodiments and are to be included within the scope of the following claims.

The invention claimed is:

1. A device comprising:
a shaft;
a distal member positioned at a distal end of the shaft, said distal member comprising:
    a forward end and a rearward end;
    a forward tip formed at the forward end of the distal member;
    a right edge and a left edge progressing rearwardly from the forward tip,
    the right edge and left edge defining a cavity therebetween and rearward of the forward tip;
    a bottom defining a bottom surface, wherein the bottom is curved from the forward tip to the rearward end,
wherein the right edge and the left edge incline at an angle of between about 35 degrees to about 40 degrees relative to a linear axis extending tangentially to the bottom surface at the forward tip to form upwardly-sloping top surfaces;
wherein the forward tip is blunt;
wherein at least a portion of the cavity is U-shaped; and
wherein at least a portion of the right edge and the left edge are configured to cut tissue as the tissue advances in the rearward direction over the right and left edges.

2. The device according to claim 1, wherein the portion of the right edge and the left edge are serrated.

3. The device according to claim 1, wherein the right edge and the left edge are curled inward as they progress rearward.

4. The device according to claim 3, wherein at a first location on the forward tip, the right edge and the left edge are positioned at a first height and oriented at a first orientation that is vertical or near vertical in relation to the bottom.

5. The device according to claim 4, wherein at a second location rearward of the first location, the right edge and the left edge are higher than at the first location and have a rotation to a second orientation between horizontal and vertical and further from vertical than the first orientation.

6. The device according to claim 5, wherein at a third location rearward of the second location, the right edge and the left edge are higher than at the second location and have a further rotation to a third orientation that is past horizontal and sloping downward toward the cavity.

7. The device according to claim 6, wherein at a fourth location rearward of the third location, the right edge and the left edge are higher than at the third location.

8. The device according to claim 6, wherein at a region that includes the third location, the right edge and the left edge are configured to cut tissue.

9. The device according to claim 8, wherein within the region, the right edge and the left edge have serrations.

10. The device according to claim 1, wherein the right edge and the left edge increase in height as they progress rearward.

11. The device according to claim 1, wherein the right edge and the left edge increase in height and rotate as they progress rearward.

12. The device according to claim 1 further comprising an aspiration lumen.

13. A system comprising the device according to claim 12 in combination with an aspiration pump connected to the aspiration lumen.

14. The system according to claim 13, wherein the aspiration pump is part of a phacoemulsification console or phacoemulsification surgical system.

15. The device according to claim 1, further comprising an irrigation lumen.

16. The device according to claim 1, further comprising an aspiration lumen and an irrigation lumen.

17. A method for using the device according to claim 1 to form an opening in trabecular meshwork tissue of an eye having a Schlemm's Canal, an anterior chamber, and a trabecular meshwork, said method comprising the steps of:
    inserting into the anterior chamber a distal portion of the device, wherein the distal portion includes the distal member;
    advancing the distal member, the forward tip first, through the trabecular meshwork and into the Schlemm's Canal; and
    advancing the distal member, the forward tip first, through the Schlemm's Canal such that at least a portion of the trabecular meshwork tissue contacts and is severed by the right edge and the left edge of the distal member.

18. The method according to claim 17, wherein the device further comprises an aspiration lumen and wherein the method further comprises aspirating tissue and/or fluid through the aspiration lumen.

19. The method according to claim 18, wherein the device further comprises an irrigation lumen and wherein the method further comprises delivering fluid into the eye through the irrigation lumen.

20. The method according to claim 19, wherein hyphema or collection of blood within the Schlemm's Canal or the anterior chamber occurs and wherein irrigation and aspiration are used to clear blood from the Schlemm's Canal or the anterior chamber.

21. The method according to claim 18, wherein the at least a portion of the trabecular meshwork tissue that is severed during the procedure is aspirated into the aspiration lumen.

22. The device of claim 1, wherein the right edge and the left edge incline at a substantially fixed angle of between about 35 degrees to about 40 degrees relative to the linear axis along their entire length.

23. The device according to claim 1, wherein a width between the right edge and the left edge increases as they progress rearward from the forward tip to the rearward end.

24. The device according to claim 23, wherein the width between the right edge and the left edge increases progressively from the forward tip to the rearward end, wherein the width is narrowest adjacent the forward tip and widest adjacent the rearward end.

* * * * *